(12) United States Patent
Liu

(10) Patent No.: US 7,470,398 B2
(45) Date of Patent: Dec. 30, 2008

(54) METHOD AND APPARATUS FOR SAMPLE EVALUATION

(76) Inventor: Xuehui Liu, 2332 S. Duluth Ave., Sioux Falls, SD (US) 57105

( * ) Notice: Subject to any disclaimer, the term of this patent is extended or adjusted under 35 U.S.C. 154(b) by 670 days.

(21) Appl. No.: 11/281,652

(22) Filed: Nov. 17, 2005

(65) Prior Publication Data

US 2007/0110623 A1    May 17, 2007

(51) Int. Cl.
  *G01N 31/22* (2006.01)
  *B01L 3/00* (2006.01)
(52) U.S. Cl. .............................. 422/58; 422/55; 422/56; 422/61; 422/68.1; 422/99; 422/102; 422/104; 436/169
(58) Field of Classification Search ............. 422/55–58, 422/61, 68.1, 69, 99, 102, 104; 436/169
  See application file for complete search history.

(56) References Cited

U.S. PATENT DOCUMENTS

| | | | |
|---|---|---|---|
| 3,895,914 A | 7/1975 | Alberty et al. | |
| 3,901,657 A | 8/1975 | Lightfoot | |
| 3,915,647 A | 10/1975 | Wright | |
| 4,125,372 A | 11/1978 | Kawai et al. | |
| 4,361,537 A | 11/1982 | Deutsch et al. | |
| 5,447,837 A | 9/1995 | Urnovitz | |
| 5,709,976 A | 1/1998 | Malhotra | |
| 6,150,178 A | 11/2000 | Cesarczyk et al. | |
| 6,555,390 B2 | 4/2003 | Chandler | |
| 6,663,831 B2 | 12/2003 | Konecke | |
| 6,669,908 B2 * | 12/2003 | Weyker et al. ................. | 422/58 |
| 6,808,682 B1 | 10/2004 | Bates et al. | |
| 2002/0085953 A1 | 7/2002 | Parker | |
| 2003/0190745 A1 | 10/2003 | Galloway et al. | |
| 2004/0018636 A1 | 1/2004 | Zhou et al. | |
| 2005/0075152 A1 | 4/2005 | Buck | |
| 2008/0206740 A1 * | 8/2008 | Skiffington et al. ............ | 435/5 |

FOREIGN PATENT DOCUMENTS

GB              2357143 A       6/2001

* cited by examiner

*Primary Examiner*—Tony G Soohoo
*Assistant Examiner*—Jameson Q Ma
(74) *Attorney, Agent, or Firm*—Frank Liebenow

(57) ABSTRACT

A specimen testing apparatus includes an outer case and an inner case that adjustably extends beyond the bottom end of the outer case. The inner case has a plurality of test strips for biologically testing a specimen, whereby a wick affixed to the bottom end of the inner case draws the specimen into each of the test strips after the inner case is extended and the wick is exposed to the specimen. A cover is provided to protect the apparatus from contamination and to seal the apparatus after exposure to the specimen.

28 Claims, 5 Drawing Sheets

METHOD AND APPARATUS FOR SAMPLE EVALUATION

FIELD OF THE INVENTION

This invention relates to a method and apparatus for evaluating test samples and more particularly, for accepting a sample of a liquid specimen on an extendable wick and transporting the sample to a multitude of test membranes.

BACKGROUND OF THE INVENTION

Various devices have been used to accept liquid biological samples, evaluate the sample and display test results by color change such as detecting AIDS, glucose, alcohol abuse, drug abuse, viruses and the like. The simplest of such are single test strips that have a chemical strip that, after dipped in a sample, undergoes a chemical reaction when exposed to the target substance. These test strips are limited in the number of tests that can be performed at one time, limit privacy and create a biological disposal issue. If a series of tests need be performed, multiple test strips are exposed to the same sample, creating a potential for confusion between the different tests and requiring disposal or storage of multiple strips. If the strips have to be retained for evidence or transported to another location, they need to be sealed in a container to prevent contamination and prevent exposure to potentially biologically hazardous materials.

Other devices have extension portions that extend into the sample, and then retract after making contact. One such device is described in U.S. Pat. No. 6,150,178 to Cesarczyk and Phildius, which is hereby incorporated by reference. This patent describes a specimen collecting and testing device that slides out of a plastic holder by pushing a shaft, passing the test membrane and exposing it to the sample. The described device is limited to one particular test. Furthermore, once the sample is collected, there is no seal to prevent leakage if this device is to be stored or transported to another location.

What is needed is a method and apparatus for specimen collecting that provides for multiple tests that are easy to read, yet are optionally protected for privacy purposes. Also needed is a specimen collecting device that is self-sealing for mailing, storage and to reduce exposure to biologically hazardous materials.

SUMMARY OF THE INVENTION

Accordingly, an objective of the present invention is to provide a specimen tester that performs multiple tests from the same sample, concurrently.

Another objective of the present invention is to provide a specimen tester that organizes multiple tests in an easy to read format.

Another objective of the present invention is to provide a specimen tester that includes a cover for preventing unwanted exposure to contaminants before the tester is exposed and prevents leakage of potentially biologically hazardous liquids after it is exposed to a specimen.

In a first embodiment, an apparatus for testing a specimen is disclosed including an outer case having a bottom end that is open with an extendable carrier adapted within it. A wick is affixed to a bottom end of the extendable carrier for accepting the specimen and a knob is rotatably coupled to a top surface of the outer case. The knob has a screw extending though threads in a top portion of the extendable carrier for extending and retracting the extendable carrier. The is at least one test membrane affixed to the carrier, visible through the outer case and interfaced with the wick member whereby the wick member is coupled to the at least one test membrane so as to transfer the specimen from the wick member to the at least one test membrane.

In another embodiment, a method for collecting and testing a specimen is disclosed including providing a test kit having an outer case, an extendable carrier adapted within the outer case, at least one test membrane affixed to the carrier and a knob rotatably coupled to a top surface of the outer case. A wick member affixed to a bottom end of the extendable carrier for accepting the specimen. The at least one test membrane is visible through the outer case and is interfaced with the wick member. The knob has a screw extending though threads in a top portion of the extendable carrier for extending and retracting the extendable carrier. The method proceeds with rotating the knob, thereby extending the wick beyond a bottom edge of the outer case, the exposing the wick to the specimen by dipping the wick into the specimen, thereby transferring the specimen from the wick to the at least one test membrane using capillary action. Finally, rotating the knob in an opposite direction, thereby retracting the wick into the carrier.

In another embodiment, an apparatus for collecting and testing a specimen is disclosed including an enclosure and an extendable carrier adapted within the enclosure. A wick is affixed to a bottom end of the extendable carrier for accepting the specimen. There is a mechanism for extending and retracting the extendable carrier and at least one test membrane is affixed to the carrier and visible through the enclosure and interfaced with the wick. The wick is coupled to the at least one test membrane so as to transfer the specimen from the wick to the at least one test membrane.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION OF THE INVENTION

Figure 1:
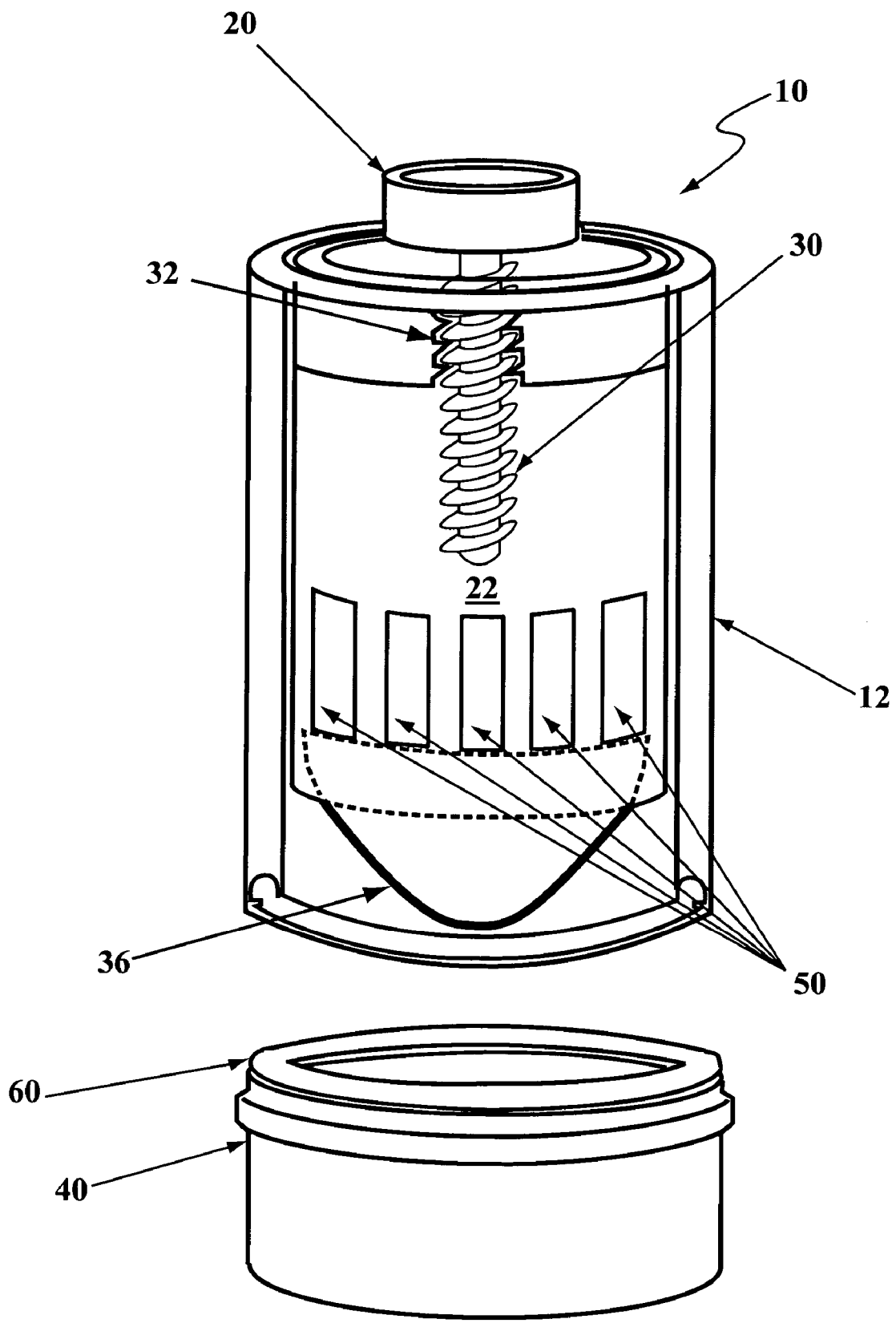
FIG. 1 illustrates a perspective view of the device of the present invention.

Reference will now be made in detail to the presently preferred embodiments of the invention, examples of which are illustrated in the accompanying drawings. Throughout the following detailed description, the same reference numerals refer to the same elements in all figures.

Referring to FIG. 1, a perspective view of the device of the present invention is shown. In the preferred embodiment, the tester 10 is of cylindrical shape, but in other embodiments, the tester is, for example, of square, rectangular, hexagonal, octagonal, pentagonal or triangular shape as the overall shape is exemplary. The tester 10 has an outer case 12 that is preferably clear or translucent to provide visibility to the individual test membranes 50. The test membranes 50 are affixed to an extendable carrier 22 and interface to the wick 36 located at the bottom of the extendable carrier 22. It is preferred that the extendable carrier 22 is shaped to match the outer case 12. For example, if the outer case 12 is hexagonal, the extendable carrier 22 is also hexagonal. In some embodiments, the shape of the extendable carrier 22 is different from the shape of the outer case 12. For example, the extendable carrier 22 is hexagonal and the outer case 12 is cylindrical.

In some embodiments, the test membranes 50 are affixed to an inside surface of the extendable carrier 22 and the extendable carrier 22 is made of a transparent or translucent material, making the test membranes 50 visible from the outside of the tester 10. In other embodiments, the test membranes 50 are inserted into bores within the extendable carrier 22 and are visible through the bores.

In some embodiments, the test membranes 50 comprise a hydrophilic microporous membrane that is treated with an agent that reacts to the presence of specific matter in the test specimen by changing color. For example, a test membrane 50 is treated with an agent that changes color upon exposure to glucose, thereby when exposed to a urine sample containing glucose, that specific test membrane changes color. Many test membranes are known in the industry and the present invention is not limited to any particular test membrane, chemical compound or test membrane construction. For an example, several test membranes are disclosed in U.S. Pat. No. 6,150,178 to Cesarczyk and Phildius. In some embodiments, the test membranes 50 include a filter layer and a drying layer, as known in the industry.

In some embodiments, the test membranes 50 are obstructed, preventing the technician who obtained the sample from seeing the results. In that embodiment, the tester is transferred to another person for evaluation, whereby the obstruction is defeated. In some embodiments, the obstruction is a layer of opaque security tape. In some embodiments, the obstruction is part of the tester and a mechanical operation must be performed to obtain access to the results. For example, the carrier 22 is moved beyond a detent that locks it in place and provides visibility to the test membranes 50.

The extendable carrier 22 is movably positioned within the outer case 12 allowing it to adjustably extend beyond the bottom edge of the outer case 12 for obtaining a biological sample. The extendable carrier 22 is extended by rotating a knob 20 whereas the knob 20 is rotatably coupled to the top of the outer case 12 and coupled to a screw or threaded shaft 30 that passes through threads 32 in the top of the carrier 22. In FIG. 1, the extendable carrier 22 is retracted so the wick 36 is above the bottom edge of the outer case 12. In a preferred embodiment, the wick 36 is made from an absorbent foam material. The wick 36 extends into the extendable carrier 22 and is in contact with the test membranes 50 so that when the wick 36 contacts a biological sample (liquid), capillary action transfers a portion of the sample to each of the test membranes 50.

A cover or lid 40 is provided to protect the test membranes from exposure to contaminations and in some embodiments, a seal 60 is provided at the interface between the outer case 12 and the cover 40 to provide a tight seal and prevent liquids from flowing into or out of the tester 10. Therefore, in some embodiments, the extendable carrier 22 is sealed by attaching the cover 40, protecting from the release of biologically hazardous materials. Once sealed, the tester can be mailed without the need for further sealing. Some testing requires the tester to be transported and retained for further testing, analysis and evidence. Additionally, in some embodiments, the top portion of the tester may also have a seal (not shown), for example, a rubber o-ring, to prevent leakage through the knob assembly. In the disclosed embodiment, the cover 40 is held in place by friction, requiring a tight fit. Any type of cover retaining mechanism is possible and the present invention is not limited to the described cover. Examples of cover retention mechanisms include a cover that is held in place by ridges, a screw cover, a hinged cover and a twist-and-lock cover. Cover attaching mechanisms are well known in the industry.

In some embodiments, the wick comprises absorbent foam. Although the foam can be molded, it is desirable that it be cut from a larger stock to preserve the cell structure. Preferred foam materials include polyethylene foam, polyvinylchloride foam, polyurethane foam, ethyl vinyl acetate foam, polyester foam, polyether foam and the like.

Figure 2:
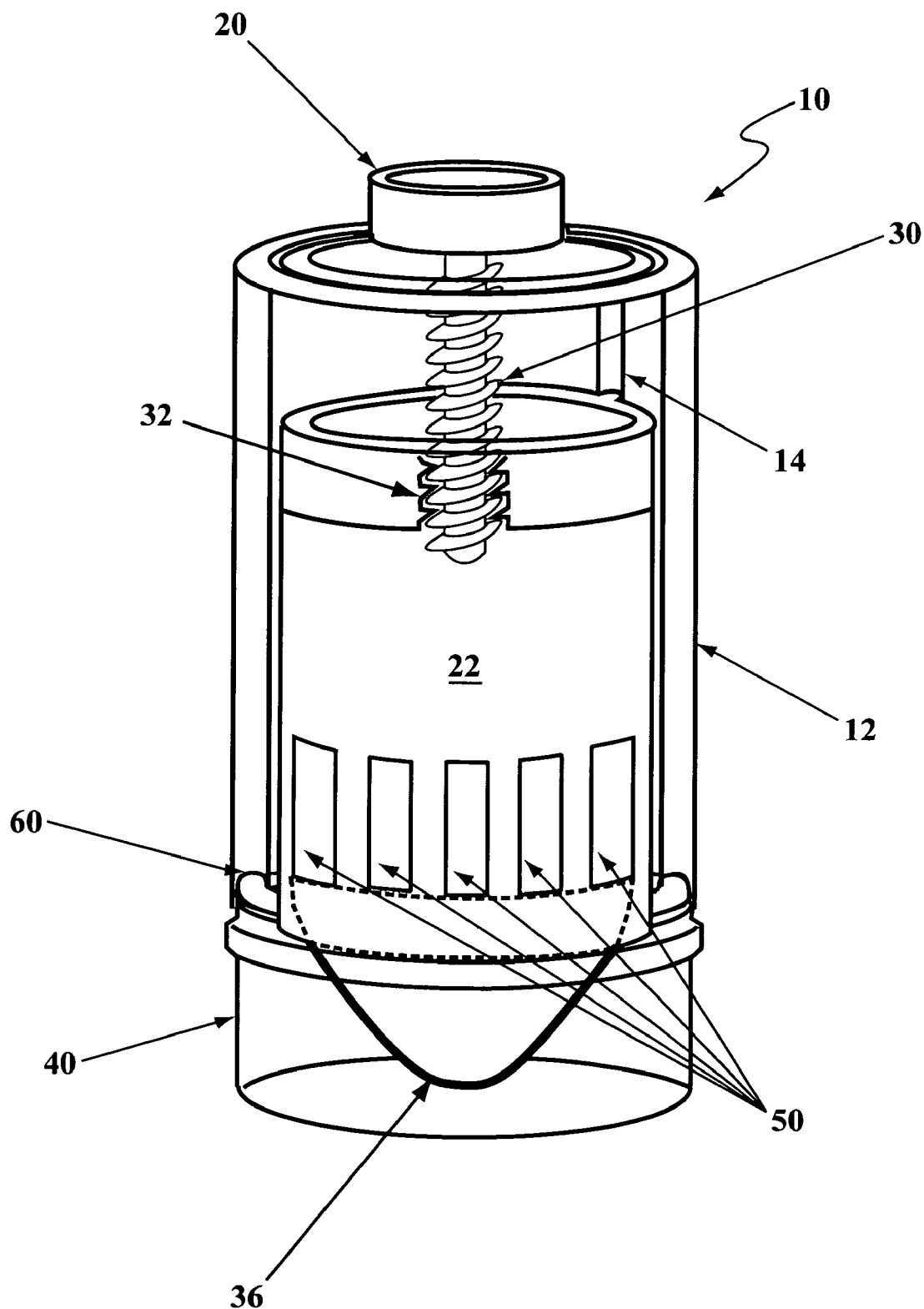
FIG. 2 illustrates a perspective view of the device of the present invention.

Referring to FIG. 2, an a perspective view of the device of the present invention is shown. As in FIG. 1, the tester 10 has an outer case 12 that is preferably clear or translucent to provide visibility to the individual test membranes 50. The test membranes 50 are affixed to an extendable carrier 22 and interface with the wick 36. The extendable carrier 22 is movably positioned within the outer case 12 allowing it to adjustably extend the wick 36 beyond the bottom edge of the outer case 12 for obtaining a sample. The extendable carrier 22 is extended by rotating a knob 20 whereas the knob 20 is rotatably coupled to the top of the outer case 12 and coupled to a threaded shaft or screw 30 that passes through threads 32 in the top of the carrier 22. In FIG. 2, the knob has not been rotated, thereby leaving the extendable carrier 22 retracted so that a wick 36 is contained within the outer case 12 and the optional cover or lid 40 is shown affixed to the tester 10. In this example, a seal 60 between the outer case 22 and the cover 40 helps prevent leakage of the specimen and helps prevent outside contamination during storage and shipping.

Figure 3:
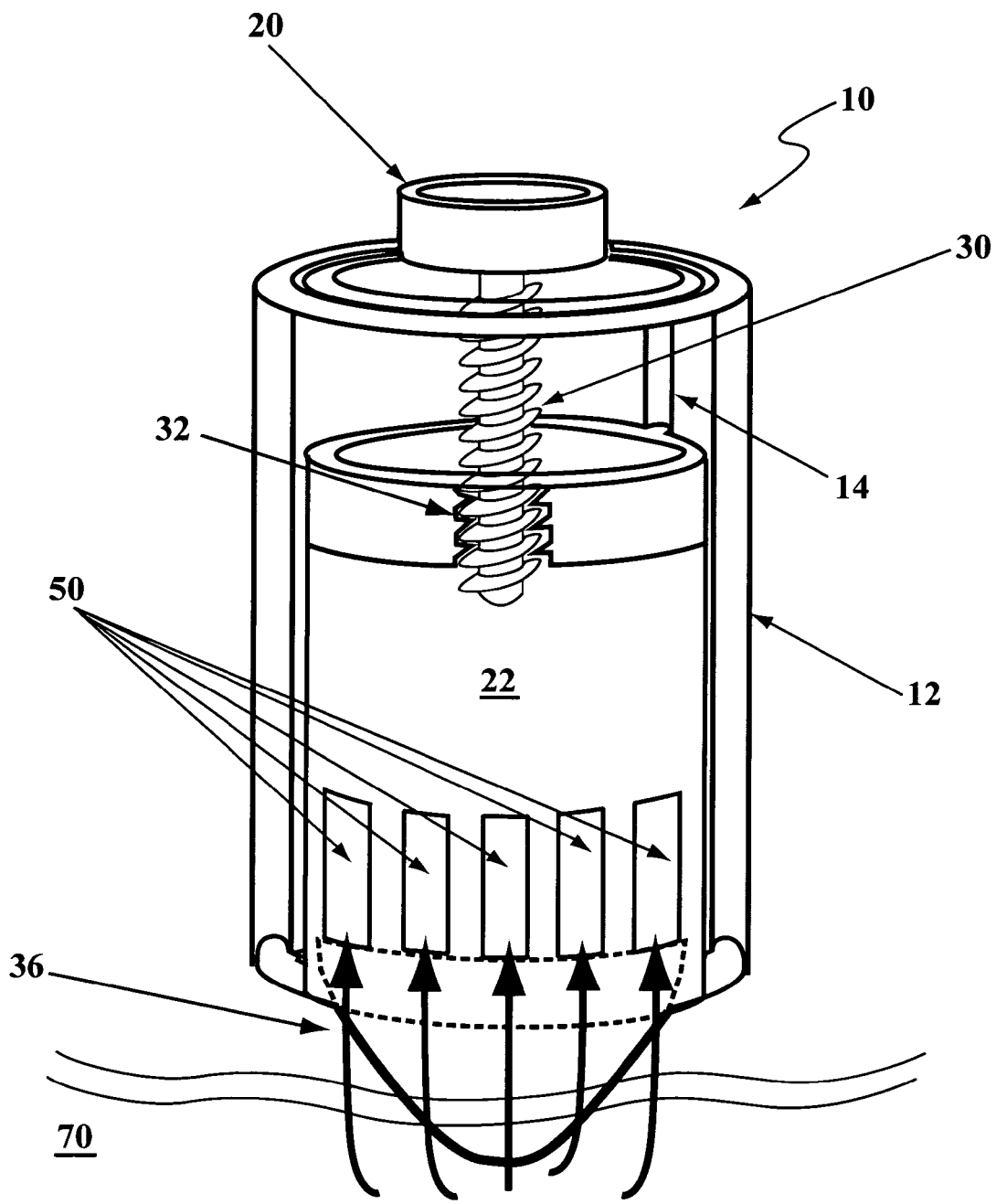
FIG. 3 illustrates a perspective view of the device of the present invention.

Referring to FIG. 3, a perspective view of the device of the present invention is shown. The tester 10 has an outer case 12 that is preferably clear or translucent to provide visibility to the individual test membranes 50. The test membranes 50 are affixed to an extendable carrier 22 and extendable carrier 22 is movably positioned within the outer case 12 allowing it to adjustably extend beyond the bottom edge of the outer case 12 for obtaining a sample. The extendable carrier 22 is extended by rotating a knob 20 whereas the knob 20 is rotatably coupled to the top of the outer case 12 and coupled to a screw or threaded shaft 30 that passes through threads 32 in the top of the carrier 22. In FIG. 3, the cover 40 (not shown) is removed and the knob has been rotated, extending the extendable carrier 22 downward so that a wick 36 extends beyond the bottom edge of the outer case 12. The wick 36 is partially submerged into a biological sample or specimen 70, for example a urine sample. The specimen 70 at least partially saturates the wick 36 and is transferred to the test membranes 50 through capillary action. After the tester 10 is exposed to the sample 70, the knob 20 is rotated to retract the extendable carrier 22 into the outer case 12 and the cover 40 (not shown in this figure) is attached, sealing the device and protecting it from contamination as well as preventing leakage of biological materials during storage or shipping of the tester 10.

Figure 4:
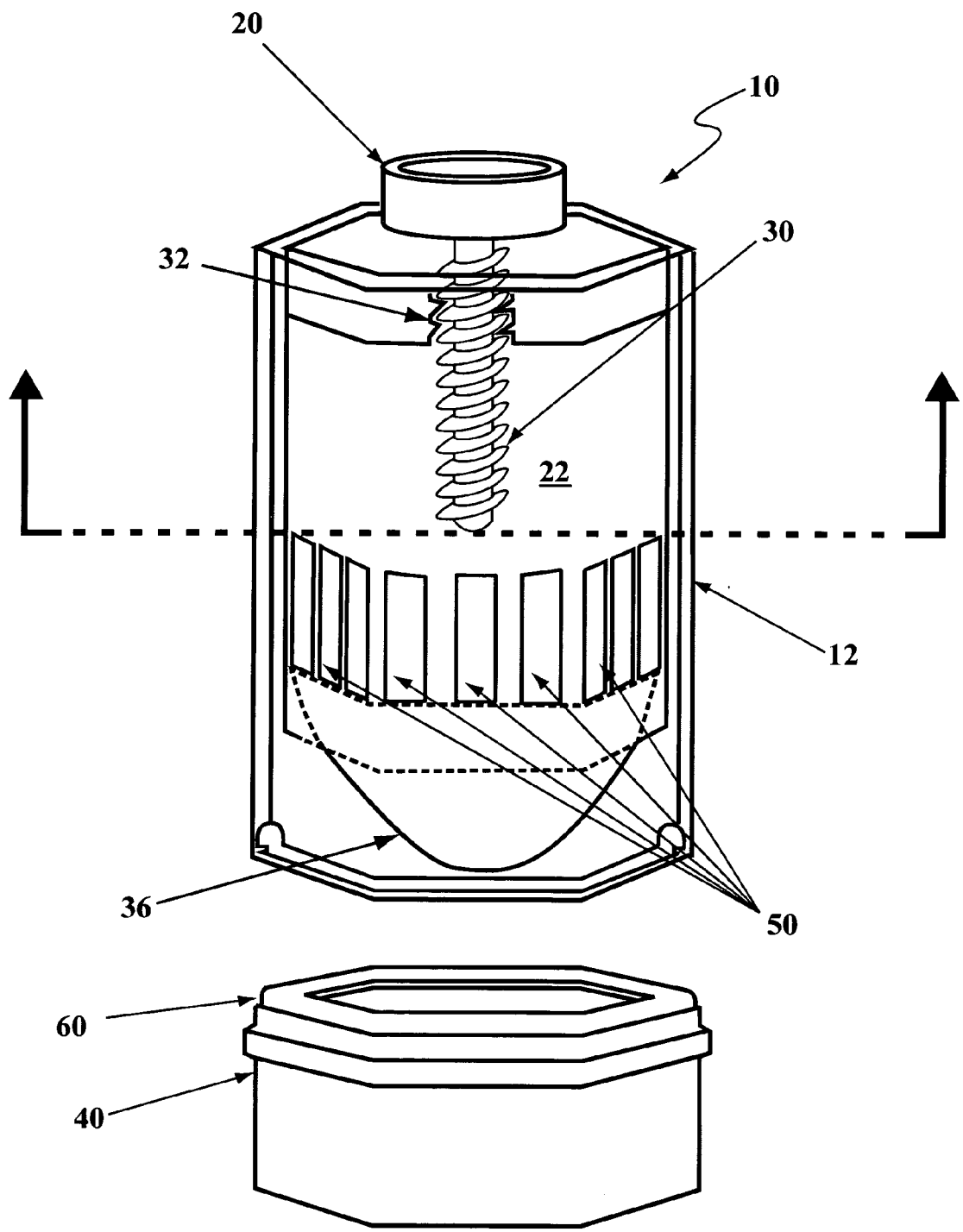
FIG. 4 illustrates a perspective view of the device of the present invention.
Figure 5:
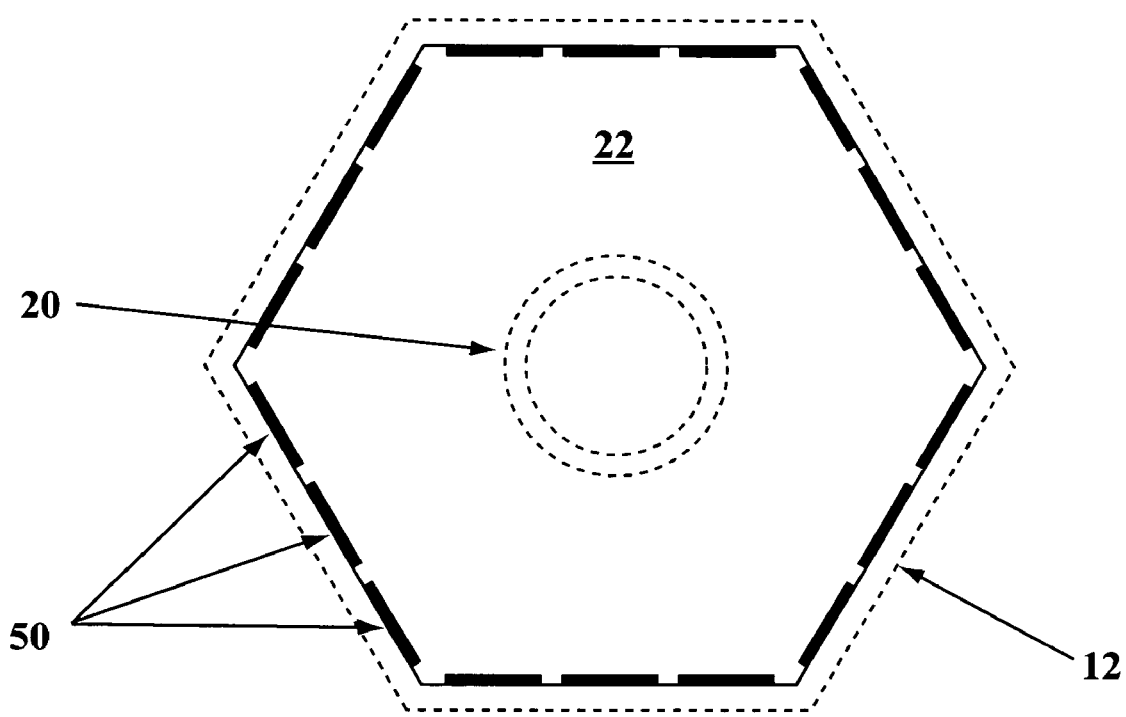
FIG. 5 illustrates a sectional view along lines 1-1 of FIG. 4 of the device of the present invention.

Referring to FIG. 4, a perspective view of the device of the present invention is shown. In this embodiment, the tester 10 is of hexagonal shape having flat sides. The tester 10 has an outer case 12 that is preferably clear or translucent to provide visibility to the individual test membranes 50. The test membranes 50 are affixed to flat sides of an extendable carrier 22 and interface to the wick 36 located at the bottom of the extendable carrier 22. It is preferred that the extendable carrier 22 is shaped to match the outer case 12. In this embodiment, the outer case 12 is hexagonal and therefore, the extendable carrier 22 is also hexagonal. In some embodiments, the shape of the extendable carrier 22 is different from the shape of the outer case 12. An example of this would be if the extendable carrier 22 is hexagonal and the outer case 12 is cylindrical.

In some embodiments, the test membranes 50 are affixed to an inside surface of the extendable carrier 22 and the extendable carrier 22 is made of a transparent or translucent material, making the test membranes 50 visible from the outside of the tester 10. In other embodiments, the test membranes 50 are inserted into bores within the extendable carrier 22 and are visible through the bores. In some embodiments, there is a non-porous fill material (not shown) within the carrier 22 and behind the test membranes 50.

In some embodiments, the test membranes 50 comprise a hydrophilic microporous membrane that is treated with an agent that reacts to the presence of specific matter in the test specimen by changing color. For example, a test membrane 50 is treated with an agent that changes color upon exposure to glucose, thereby when exposed to a urine sample containing glucose, that specific test membrane changes color. Many test membranes are known in the industry and the present invention is not limited to any particular test membrane, chemical compound or test membrane construction. For an example, several test membranes are disclosed in U.S. Pat. No. 6,150,178 to Cesarczyk and Phildius. In some embodiments, the test membranes 50 include a filter layer and a drying layer, as known in the industry.

In some embodiments, the test membranes 50 are obstructed, preventing the technician who obtained the sample from seeing the results. In that embodiment, the tester is transferred to another person for evaluation, whereby the obstruction is defeated. In some embodiments, the obstruction is a layer of opaque security tape. In some embodiments, the obstruction is part of the tester and a mechanical operation must be performed to obtain access to the results. For example, the carrier 22 is moved beyond a detent that locks it in place and provides visibility to the test membranes 50.

The extendable carrier 22 is movably positioned within the outer case 12 allowing it to adjustably extend beyond the bottom edge of the outer case 12 for obtaining a biological sample. The extendable carrier 22 is extended by rotating a knob 20 whereas the knob 20 is rotatably coupled to the top of the outer case 12 and coupled to a screw or threaded shaft 30 that passes through threads 32 in the top of the carrier 22. In FIG. 1, the extendable carrier 22 is retracted so the wick 36 is above the bottom edge of the outer case 12. In a preferred embodiment, the wick 36 is made from an absorbent foam material. The wick 36 extends into the extendable carrier 22 and is in contact with the test membranes 50 so that when the wick 36 contacts a biological sample (liquid), capillary action transfers a portion of the sample to each of the test membranes 50.

A cover or lid 40 is provided to protect the test membranes from exposure to contaminations and in some embodiments, a seal 60 is provided at the interface between the outer case 12 and the cover 40 to provide a tight seal and prevent liquids from flowing into or out of the tester 10. Therefore, in some embodiments, the extendable carrier 22 is sealed by attaching the cover 40, protecting from the release of biologically hazardous materials. Once sealed, the tester can be mailed without the need for further sealing. Additionally, in some embodiments, the top portion of the tester may also have a seal (not shown), for example, a rubber o-ring, to prevent leakage through the knob assembly. In the disclosed embodiment, the cover 40 is held in place by friction, requiring a tight fit. Any type of cover retaining mechanism is possible and the present invention is not limited to the described cover. Examples of cover retention mechanisms include a cover that is held in place by ridges, a screw cover, a hinged cover and a twist-and-lock cover. Cover attaching mechanisms are well known in the industry.

Equivalent elements can be substituted for the ones set forth above such that they perform in substantially same manner in substantially the same way for achieving substantially the same result.

It is believed that the system and method of the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. An apparatus for collecting and testing a specimen, the apparatus comprising:
   an outer case, a bottom end of the outer case being open;
   an extendable carrier adapted within the outer case;
   a wick member affixed to a bottom end of the extendable carrier adapted to accept the specimen;
   a knob rotatably coupled to a top surface of the outer case, the knob having a screw extending though threads in a top portion of the extendable carrier, whereas rotation of the knob extends and retracts the extendable carrier; and
   at least one test membrane affixed to a side surface of the extendable carrier, the at least one test membrane visible through the outer case and the at least one test membrane interfaced with the wick member,
   whereby the wick member is coupled to the at least one test membrane so as to transfer the specimen from the wick member to the at least one test membrane.

2. The apparatus for collecting and testing a specimen of claim 1, further comprising:
   a lid removably adapted to the bottom end of the outer case, the lid providing a cover for the wick member.

3. The apparatus for collecting and testing a specimen of claim 1, wherein the outer case and the extendable carrier are cylindrically shaped.

4. The apparatus for collecting and testing a specimen of claim 1, wherein the wick member comprises an absorbent foam rubber.

5. The apparatus for collecting and testing a specimen of claim 2, further comprising a seal adapted between the outer case and the lid, preventing leakage when the lid is affixed to the outer case.

6. The apparatus for collecting and testing a specimen of claim 1, wherein rotation of the knob in a first direction extends the extendable carrier and wick member beyond the bottom end of the outer case and rotation of the knob in a second direction retracts the extendable carrier and the wick member into the outer case.

7. The method for collecting and testing a specimen, the method comprising:
   providing a test kit, the test kit comprising:
      an outer case;
      an extendable carrier adapted within the outer case;
      a wick member affixed to a bottom end of the extendable carrier for accepting the specimen;
      at least one test membrane affixed to a side surface of the extendable carrier, the at least one test membrane visible through the outer case and the at least one test membrane interfaced with the wick member and a knob rotatably coupled to a top surface of the outer case, the knob having a screw extending though threads in a top portion of the extendable carrier, whereas rotation of the knob extends and retracts the extendable carrier;

rotating the knob in a first direction, thereby extending the wick member beyond a bottom edge of the outer case;

exposing the wick member to the specimen;

transferring the specimen from the wick member to the at least one test membrane using capillary action; and rotating the knob in an opposite direction, thereby retracting the wick member into the carrier.

8. The method for collecting and testing a specimen of claim 7, further comprising:

placing a lid over a bottom end of the outer case.

9. The method for collecting and testing a specimen of claim 8, the test kit further comprising a seal adapted between the bottom end of the outer case and the lid, preventing leakage when the lid is affixed to the outer case.

10. The method for collecting and testing a specimen of claim 7, wherein the outer case and the extendable carrier are cylindrically shaped.

11. The method for collecting and testing a specimen of claim 7, wherein the wick member comprises an absorbent foam rubber.

12. An apparatus for collecting and testing a specimen, the apparatus comprising:

an enclosure means, a bottom end of the enclosure means being open;

an extendable carrier means adapted within the enclosure means;

a wick means affixed to a bottom end of the extendable carrier means for accepting the specimen;

a means for extending and retracting the extendable carrier; and at least one test membrane affixed to a side surface of the carrier means, the at least one test membrane visible through the enclosure means and interfaced with the wick means, whereby the wick means is coupled to the at least one test membrane so as to transfer the specimen from the wick means to the at least one test membrane.

13. The apparatus for collecting and testing a specimen of claim 12, further comprising:

a means for sealing the enclosure means removably affixed to the bottom end of the enclosure means and providing a cover for the wick means.

14. The apparatus for collecting and testing a specimen of claim 13, further comprising a seal adapted between the enclosure means and the means for sealing, preventing leakage when the means for sealing is affixed to the enclosure means.

15. The apparatus for collecting and testing a specimen of claim 12, wherein the enclosure means and the extendable carrier means are cylindrically shaped.

16. The apparatus for collecting and testing a specimen of claim 12, wherein the wick means comprises an absorbent foam rubber.

17. The apparatus for collecting and testing a specimen of claim 12, wherein the means for extending and retracting is a knob rotatably coupled to the enclosure means and coupled to a threaded shaft, the threaded shaft passing through threads in the extendable carrier means.

18. The apparatus for collecting and testing a specimen of claim 17, whereas rotation of the knob in a first direction extends the extendable carrier means and the wick means beyond the bottom end of the enclosure means and rotation of the knob in an opposite direction retracts the extendable carrier means and the wick means into the enclosure means.

19. An apparatus for collecting and testing a specimen, the apparatus comprising:

an enclosure means having a top surface, a bottom edge and at least three sides;

an extendable carrier means adapted within the enclosure means;

a wick means affixed to a bottom end of the extendable carrier means for accepting the specimen;

a means for extending and retracting the extendable carrier; and a plurality of test membranes, each of the plurality of test membranes affixed to one of the at least three sides and the plurality of test membranes visible through the enclosure means and the plurality of test membranes interfaced with the wick means, whereby the wick means is coupled to the plurality of test membranes so as to transfer the specimen from the wick means to the plurality of test membranes.

20. The apparatus for collecting and testing a specimen of claim 19, further comprising:

a means for sealing the enclosure means removably affixed to the bottom edge of the enclosure means and providing a cover for the wick means.

21. The apparatus for collecting and testing a specimen of claim 20, further comprising a seal adapted between the bottom edge of the enclosure means and the means for sealing, preventing leakage when the means for sealing is affixed to the enclosure means.

22. The apparatus for collecting and testing a specimen of claim 19, wherein the enclosure means and the extendable carrier means are cylindrically shaped.

23. The apparatus for collecting and testing a specimen of claim 19, wherein the enclosure means and the extendable carrier means are pentagonally shaped.

24. The apparatus for collecting and testing a specimen of claim 19, wherein the enclosure means and the extendable carrier means are hexagonally shaped.

25. The apparatus for collecting and testing a specimen of claim 19, wherein the enclosure means and the extendable carrier means are octagonally shaped.

26. The apparatus for collecting and testing a specimen of claim 19, wherein the wick means comprises an absorbent foam rubber.

27. The apparatus for collecting and testing a specimen of claim 19, wherein the means for extending and retracting is a knob rotatably coupled to the top surface of the enclosure means, the knob is coupled to a threaded shaft, the threaded shaft passing through threads in the extendable carrier means.

28. The apparatus for collecting and testing a specimen of claim 27, whereas rotation of the knob in a first direction extends the extendable carrier means and the wick means beyond the bottom end of the enclosure means and rotation of the knob in an opposite direction retracts the extendable carrier means and the wick means into the enclosure means.

* * * * *